US011255079B2

(12) United States Patent
Takahashi

(10) Patent No.: US 11,255,079 B2
(45) Date of Patent: Feb. 22, 2022

(54) FECES SAMPLING TOOL AND FECES SAMPLING TOOL MANUFACTURING DEVICE

(71) Applicant: TAKAHASHI KEISEI CORPORATION, Yamagata (JP)

(72) Inventor: Mitsuhiro Takahashi, Yamagata (JP)

(73) Assignee: Takahashi Keisei Corporation, Yamagata (JP)

( * ) Notice: Subject to any disclaimer, the term of this patent is extended or adjusted under 35 U.S.C. 154(b) by 445 days.

(21) Appl. No.: 16/097,223

(22) PCT Filed: Oct. 31, 2016

(86) PCT No.: PCT/JP2016/082192
§ 371 (c)(1),
(2) Date: Oct. 26, 2018

(87) PCT Pub. No.: WO2017/187657
PCT Pub. Date: Nov. 2, 2017

(65) Prior Publication Data
US 2019/0093331 A1 Mar. 28, 2019

(30) Foreign Application Priority Data
Apr. 26, 2016 (JP) .............................. JP2016-088647

(51) Int. Cl.
*E03D 11/13* (2006.01)
*G01N 1/04* (2006.01)
(Continued)

(52) U.S. Cl.
CPC .............. *E03D 11/13* (2013.01); *A47K 13/24* (2013.01); *E03D 9/00* (2013.01); *G01N 1/04* (2013.01); *G01N 33/48* (2013.01)

(58) Field of Classification Search
CPC ........... A47K 13/24; E03D 11/13; E03D 9/00; G01N 1/04; G01N 33/48
(Continued)

(56) References Cited

U.S. PATENT DOCUMENTS 4,445,235 A * 5/1984 Slover ................ A61B 10/0038
4/144.1
2011/0275954 A1* 11/2011 Babcock ............ A61B 10/0038
600/562
(Continued)

FOREIGN PATENT DOCUMENTS

DE 20316617 U1 * 2/2004 ......... A61B 10/0038
JP 09005318 A * 1/1997
(Continued)

*Primary Examiner* — Nimeshkumar D Patel
*Assistant Examiner* — Nashmiya S Fayyaz
(74) *Attorney, Agent, or Firm* — Osha Bergman Watanabe & Burton LLP

(57) ABSTRACT

[PROBLEM TO BE SOLVED]
The feces sampling tool which paper jams such as the drain pipe do not produce even if it is canceled on a flushing toilet stool after use is offered.
[SOLUTION]
The cup body C and a pair of band portions B 1 and B 2 extending in the left and right direction from the upper edge of the cup body C are integrated by press die to constitute the feces sampling tool 1. The cup body C is suspended in the toilet stool by band portions B 1, B 2.
The band portions B 1, B 2 are configured to be narrower than the width of the cup body C. The cup body C and the band portions B 1 and B 2 are laminated by laminating a single piece of water-soluble/water-disintegratable paper, or by combining a single sheet or a plurality of water-soluble and water-disintegratable paper.

16 Claims, 10 Drawing Sheets

(51) Int. Cl.
*E03D 9/00* (2006.01)
*A47K 13/24* (2006.01)
*G01N 33/48* (2006.01)

(58) Field of Classification Search
USPC .................................................. 73/864.91
See application file for complete search history.

(56) References Cited

U.S. PATENT DOCUMENTS

| 2013/0195523 A1* | 8/2013 | Yamaji | G03G 15/2025 |
| | | | 399/329 |
| 2017/0030757 A1* | 2/2017 | Jaffrey | E21B 33/06 |
| 2019/0239862 A1* | 8/2019 | Suehiro | A61B 10/0038 |

FOREIGN PATENT DOCUMENTS

| JP | 09061423 A | * | 3/1997 |
| JP | 2015135296 A | * | 7/2015 |

* cited by examiner (A)

(B)

(A)

(B)

(A)

(B)

(A)

(B)

(A)

(B)

(A)

(B)

x1-x1 CROSS SECTION
(C)

x2-x2 CROSS SECTION
(D)

(A)

x1-x1 CROSS SECTION
(B)

x2-x2 CROSS SECTION
(C)

FECES SAMPLING TOOL AND FECES SAMPLING TOOL MANUFACTURING DEVICE

TECHNICAL FIELD

The present invention relates to a water-soluble or water-decomposable feces sampling tool which does not cause jamming of a drainage pipe even when flushed into a flush toilet.

BACKGROUND ART

Conventionally, a feces sampling tool disclosed in Patent Document 1 are known.

FIG. 9 is a perspective view drawing showing a conventional sampling unit 91, and FIG. 10 is a drawing showing a usage mode of the tool 91.

As shown in a usage drawing of FIG. 10, both ends of the stool 91 are affixed to the left and right surfaces of an upper edge of a rim portion 921 of a toilet stool 92.

FIG. 10 (A) is a plan view. FIG. 10 (B) is a cross-sectional view taken along the line X1-X1 (front view) in FIG. 10 (A). FIG. 10 (C) is a cross-sectional view (side view) taken along line X2-X2 in FIG. 10 (A).

As shown in FIG. 9, the feces sampling tool 91 comprises a paper cup body 911 and paper band portions 912a, 912b extending in left-right direction.

The cup body 911 and the band portions 912a, 912b are integrally formed by pressing a plurality of sheets of paper.

An adhesive layers 913a and 913b are formed on the lower surface of each edge of the band portions 912a and 912b (the end portion on the side opposite to the cup body 911).

The band portions 912a, 912b are attached to left and right of the upper edge of the rim portion 921 of the toilet stool 92.

Although not shown, the band portions 912 a, 912 b can also be attached to the left and right of the upper edge of the toilet seat 922 of the toilet stool 92.

In the stool sampling by the feces sampling tool 91 shown in FIG. 9, the stools are sampled by the cup body 911, so that it is possible to prevent the sampling error occurring when stools are hard.

The feces sampling tool 91 must have strength such that the cup body 911 and the band portions 912a, 912b are not broken due to the weight of a stool at the time of taking a stool.

Therefore, in the feces sampling tool 91, for increasing the strength of the cup body 911, the thickness of the paper constituting the feces sampling tool 91 is made thicker, or the number of laminated sheets of paper is increased.

On the other hand, it is necessary for the feces sampling tool 91 to be able to flush the whole (the cup body 911, the band portions 912a, 912b) after the bowel movement. For this reason, the feces sampling tool 91 must be either immediate-water-soluble or immediate-water-disintegratable.

Invalidating Art Classic

Patent Documents

JP2015-135,296
[Patent Documents 1]

DISCLOSURE OF THE INVENTION

Problem to be Solved by the Invention

However, if the thickness of the paper is increased or the number of laminated sheets is increased in the feces sampling tool 91, immediate water-soluble or hydrolysis is not performed, and therefore a problem arises that the paper jam occurs in the drain pipe.

Particularly, in Asian countries other than Japan, the drainage pipe diameter is often small, so paper jamming is more likely to occur.

The object of the present invention is to provide a water-soluble or water-decomposable (also referred to as "water-soluble/water-decomposable") sampling device.

Means to Solve the Problem

The present invention is summarized as follows.

[1]

A feces sampling tool comprising a central rectangular area and two side rectangular areas symmetrically formed on left and right of the central rectangular region,
  wherein, a sampling portion is formed in the central rectangular area,
  a band portion is formed in each of the two side rectangular areas,
  the sampling portion and the band portions are made of one or a plurality of water-soluble or water-disintegratable paper,
  each part of the band portions is stuck on left and right upper surfaces of a toilet seat or left and right upper surfaces of a rim portion, whereby the sampling portion is suspended in a toilet stool,
  a weight per unit area of the side rectangular area is 4/5 or less of a weight per unit area of the central rectangular area.

[2]

A feces sampling tool comprising a sampling portion and two band portions symmetrically formed on left and right sides of the sampling portion,
  wherein the sampling portion and the band portions are made of one or a plurality of water-soluble or water-disintegratable paper,
  each part of the band portions is stuck on the left and right upper surfaces of a toilet seat or left and right upper surfaces of a rim portion, whereby the sampling portion is suspended in a toilet stool,
  a vertical width of the band portion is formed narrower than the vertical width of the sampling portion.

In the present invention, the term "water-soluble" means a property that when the toilet paper or the like is wetted with water, it is decomposed to lose its strength and decomposes, and the term "water decomposability" means maintaining a constant strength (wet strength) It means a property to break down finely when added.

Effect of the Invention

The feces sampling tool of the present invention does not cause clogging of paper such as a drain pipe even if it is flowed into a flush toilet after use.

BEST MODE FOR CARRYING OUT THE INVENTION

Figure 1:
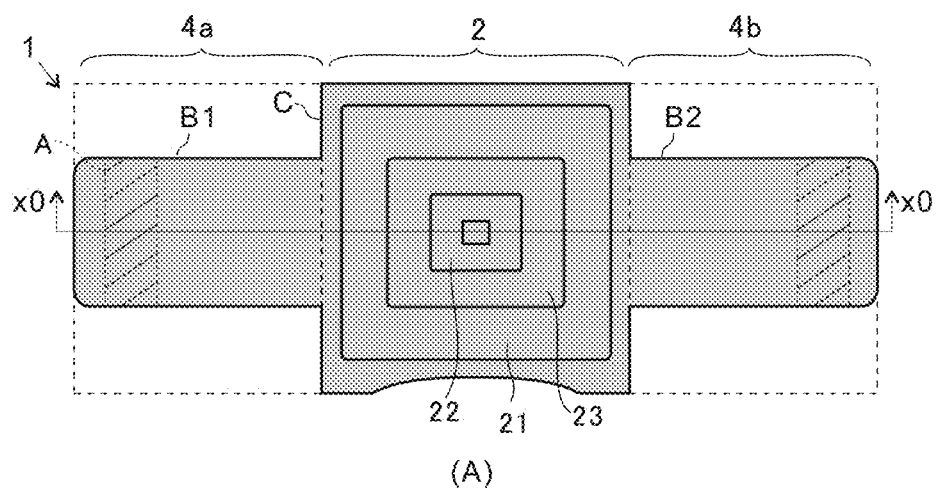
FIG. 1 is a view showing a first embodiment of the feces sampling tool according to the present invention.
Figure 1:
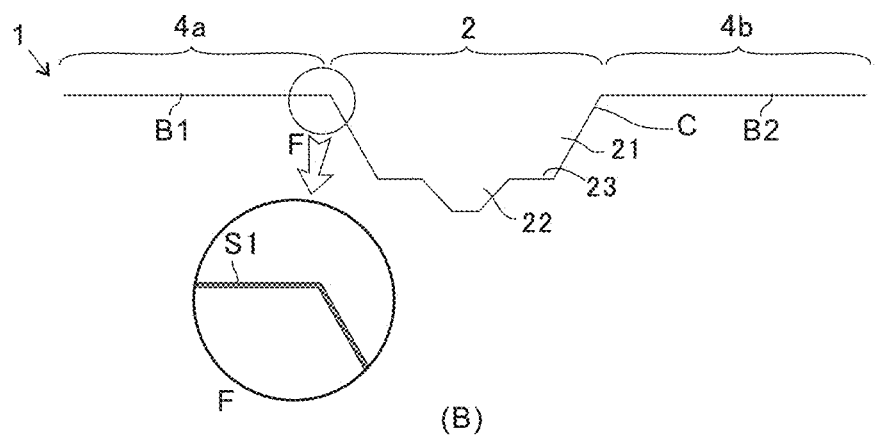

FIG. 1 is a figure showing the first embodiment of a feces sampling tool according to the present invention.

FIG. 1 (A) shows a plan view of the feces sampling tool. FIG. 1 (B) shows a sectional view of X0-X0 in FIG. 1 (A). In FIG. 1 (B), extended a figure F is added.

In FIG. 1 the feces sampling tool 1 is comprised of a central rectangular area 2 (a sampling portion) and a pair of the side rectangular areas 4a, 4b provided on either side of the central rectangular areas 2.

The center rectangular area 2 includes a cup body C.

The feces sampling tool 1 of FIG. 1 consists of a water-soluble paper or water-disintegrable paper.

In FIG. 1, each width of the band portions B1, B2 is narrower than a width of the cup body C.

In the cup body C, the whole forms a pyramid configuration with a plurality of stages.

A flange 23 is formed in an area of between the first stage 21 (the stool receiver) and the second stage 22.

The cup body C and the band portions B1, B2 are formed integrally by heat pressing.

A right edge of the cup body C continues with the band portion B1, a left edge of the cup body C continues with the band portion B2.

The configuration of the cup body C can be a triangular pyramid, a polygonal pyramid, a triangular truncated pyramid or a polygonal truncated pyramid.

In FIG. 1 the plan view of the cup body C is a quadrangle.

An adhesive layer A is formed on the underside of the band portion B1, B2.

The adhesive layer A is water-soluble or water-disintegrable.

In use of the feces sampling tool 1, the band portion B1, B2 are affixed to the left and right surfaces of the toilet seat.

Figure 7:
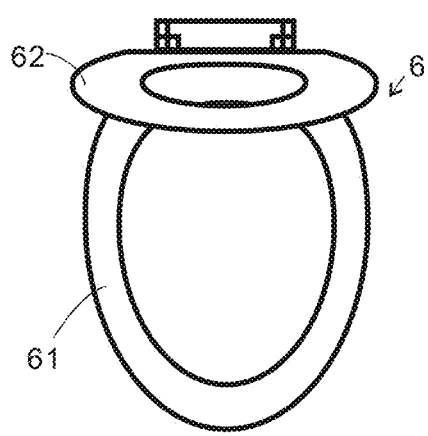
FIG. 7 is a view showing a use form of the feces sampling tool 1 shown in FIGS. 1 to 6.
Figure 7:
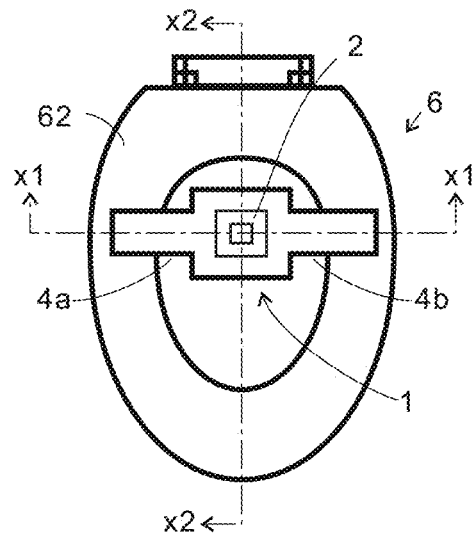
Figure 7:
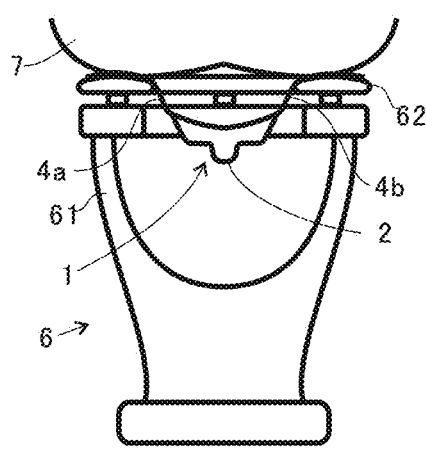
Figure 7:
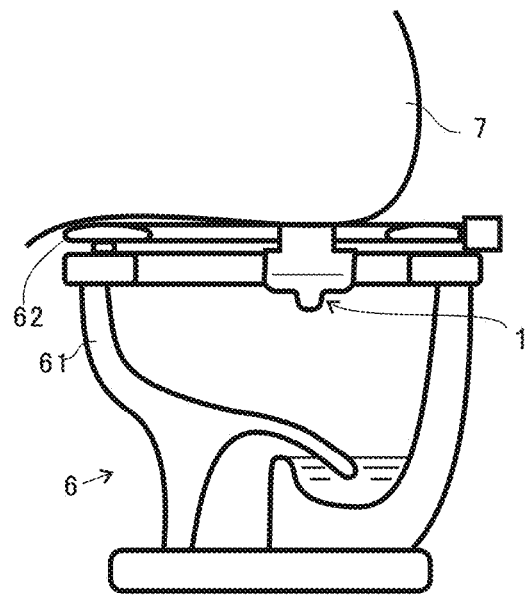

(Please refer to the toilet stool 6 of FIG. 7 and the toilet seat 62.)

Note that the band portion B1, B2 can be stuck to the right and left face of the rim portion of the toilet stool.

Figure 2:
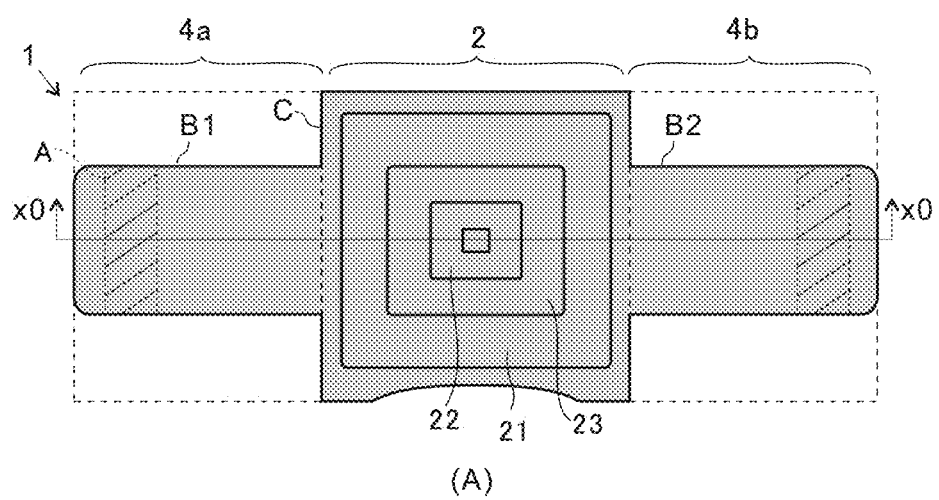
FIG. 2 is a drawing showing a first modification of the first embodiment.
Figure 2:
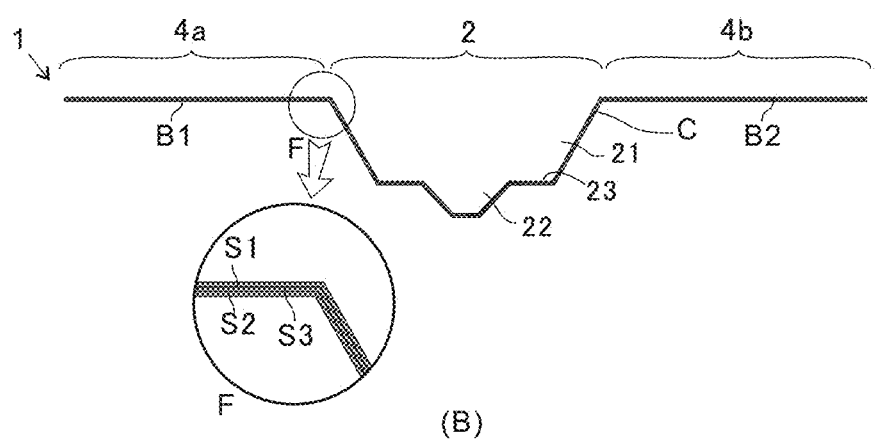

FIG. 2 is a figure showing the first alternative of the feces sampling tool 1.

FIG. 2 (A) shows a plan view of the feces sampling tool. FIG. 2 (B) shows a sectional view of X0-X0 in (A). In FIG. 2(B), extended a figure F is added.

The plan view of the feces sampling tool 1 of FIG. 2 is the same as the plan view of the feces sampling tool 1 of FIG. 1.

In the feces sampling tool 1 of FIG. 2, the number of sheets of the water-soluble paper or the water-disintegrable paper of central rectangular area 2 and the side rectangular area 4a, 4b is three pieces.

Figure 3:
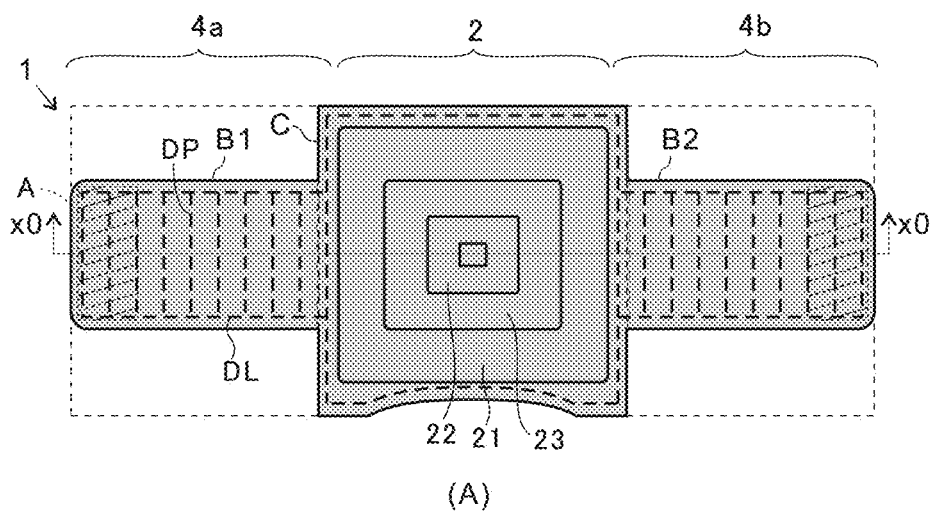
FIG. 3 is a drawing showing a second modification of the first embodiment.
Figure 3:
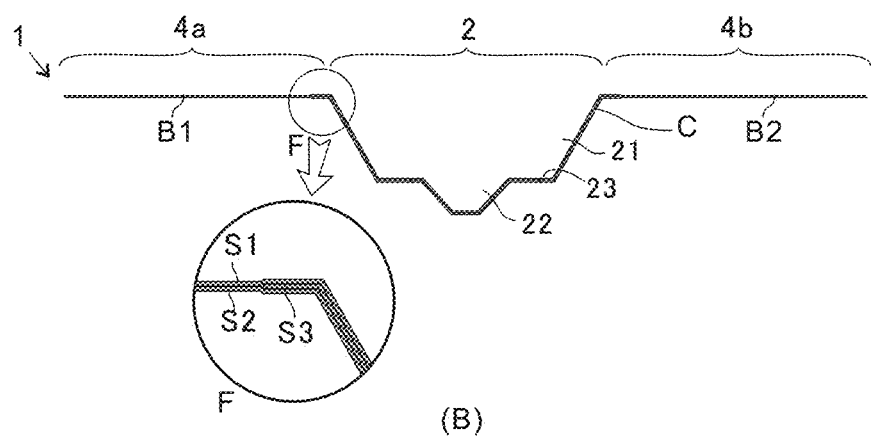

FIG. 3 (A) shows a plan view of the feces sampling tool. FIG. 3 (B) shows a sectional view of X0-X0 in (A). In FIG. 3 (B), extended a figure F is added.

In the feces sampling tool 1 of FIG. 3, the number of sheets of the water-soluble paper or the water-disintegrable paper of central rectangular area 2, the number of sheets of the water-soluble paper or the water-disintegrable paper of the side rectangular area 4a, 4b is two pieces.

That is, in feces sampling tool 1 of FIG. 3, the paper S3 which the longitudinal width is short is put between the two papers (S1, S2) which the longitudinal width is long.

The middle rectangular area 2 has a thickness of a stuck of the papers S1, S2 and S3, and each of the side rectangular areas 4a, 4b has a thickness of a stuck of the papers S1 and S2.

In the feces sampling tool 1 of FIG. 3, because the central rectangular area 2 is thick, the cup body C is not broken.

The feces sampling tool 1 of FIG. 3 is lighter than the feces sampling tool 1 of FIG. 2.

In FIG. 3, the hemming DL are formed around the cup body C and around the band portions B1, B2.

The hemming DL are formed of the broken lines shaped high press pressure portions.

Even more particularly, the pattern DP comprising the broken lines is formed in all of the band portions B1, B2.

In the present embodiment, the pattern DP is a parallel-lines pattern, but other patterns such as a lattice pattern may be used.

The hemming DL or the pattern DP may be formed of the continued lines shaped high-pressed portions.

All or a part of the hemming DL or the pattern DP may be formed of the intermittent lines shaped high-pressed portions.

Further, all or a part of the hemming DL or the pattern DP may be perforations in which the penetrating portions are intermittent.

In the feces sampling tool 1 of FIG. 3, due to the hemming DL or the pattern DP, water-soluble paper or water-disintegrable paper constituting the feces sampling tool 1 is difficult to peel off. Therefore, the strength of the cup C body and the band portion B1, B2 are kept.

Figure 4:
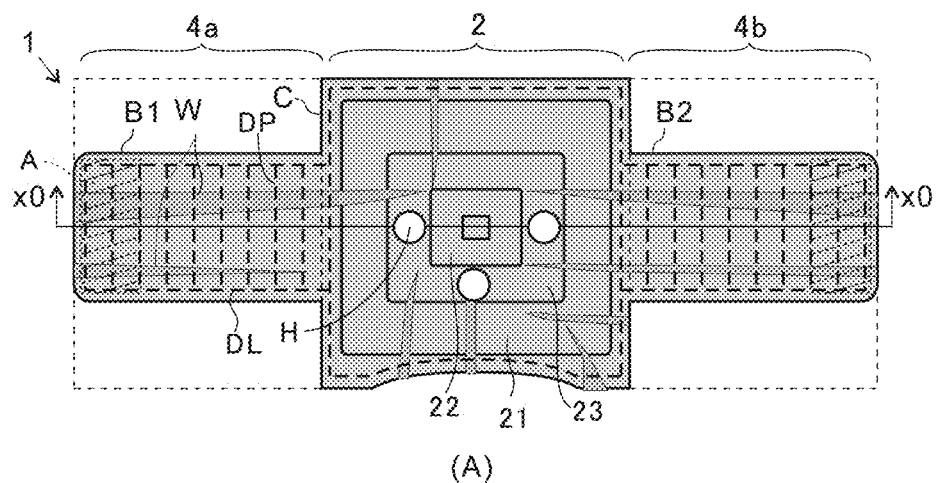
FIG. 4 is a drawing showing a third modification of the first embodiment.
Figure 4:
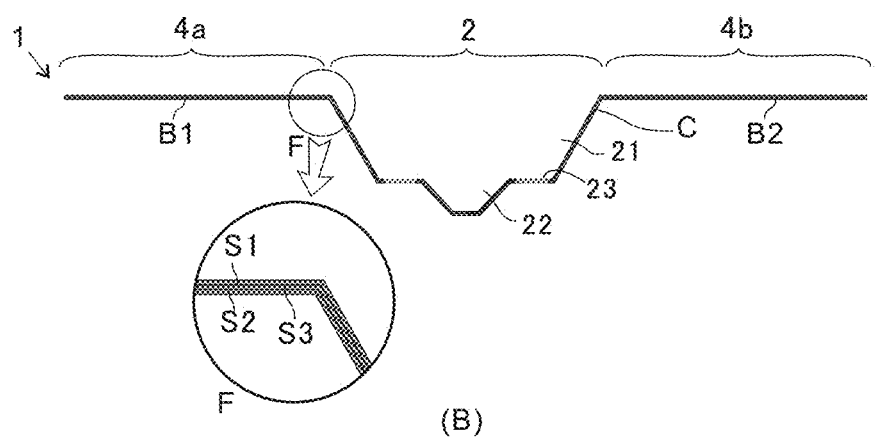

FIG. 4 (A) shows a plan view of the feces sampling tool. FIG. 4 (B) shows a sectional view of X0-X0 in (A). In FIG. 4 (B), extended a figure F is added.

In the feces sampling tool 1 of FIG. 4, a plurality of wrinkles W are formed in the cup body C and the band portions B 1, B 2.

These wrinkles W strengthen the strength of the cup body C and the band portions B 1, B 2.

In the feces sampling tool 1 of FIG. 4, the watery feces discharge hole H is formed in the flange 23 of the cup body C.

In the feces sampling tool 1 of FIG. 4, the number of water-soluble or water-disintegratable paper used in the central rectangular area 2 and the side rectangular areas 4 a, 4 b is three.

In FIG. 3, the bordering DL and the pattern DP are formed around the cup body C and around the band portions B1, B2.

In the feces sampling tool 1 of the first embodiment, since the vertical width of the band portions B 1 and B 2 is shorter than the vertical width of the cup body C, paper jamming is unlikely to occur.

From the above explanation, it will be understood that in the feces sampling tool 1 of the present invention, it is difficult for a paper jam such as a drain pipe to occur.

Figure 5:
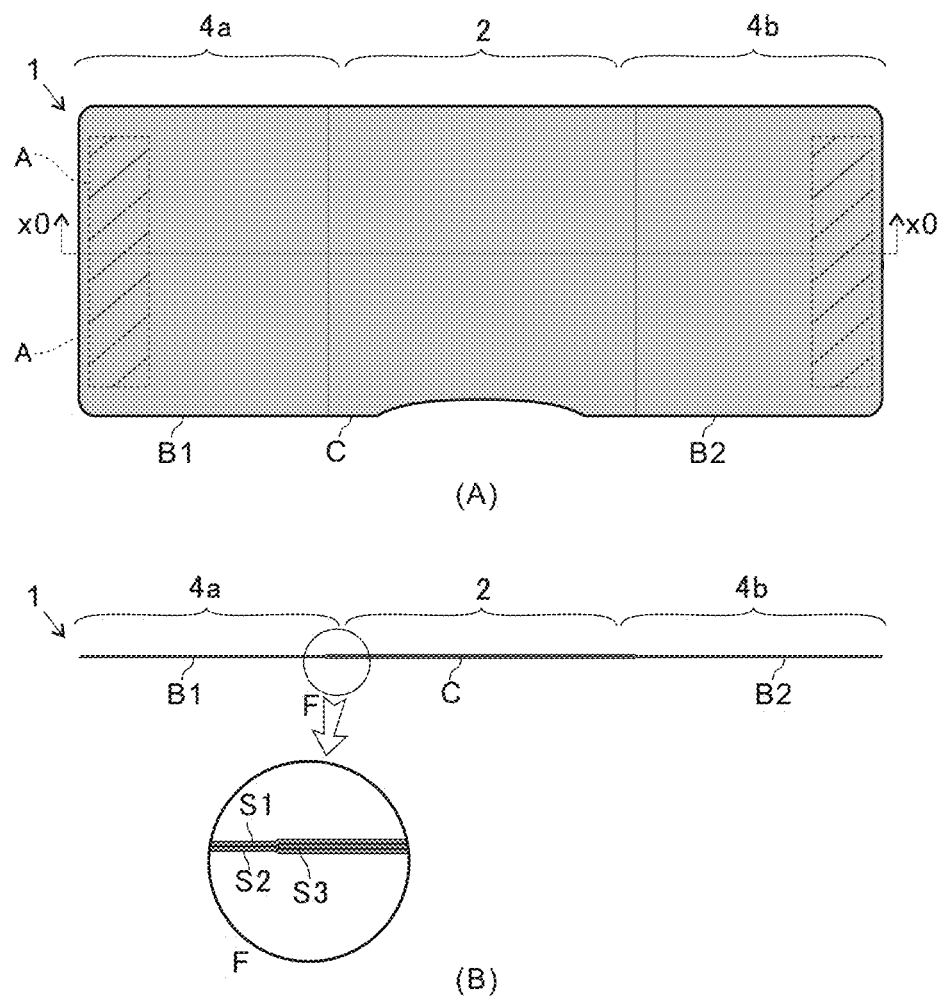
FIG. 5 is a view showing a second embodiment of the feces sampling tool according to the present invention.

FIG. 5 (A) shows a plan view of the feces sampling tool. FIG. 5 (B) shows a sectional view of X0-X0 in (A). In FIG. 5 (B), extended a figure F is added.

In FIG. 5, the feces sampling tool 1 is comprised of the central rectangular areas 2 (a sampling portion) and a pair of the side rectangular areas 4a, 4b provided on either side of the central rectangular areas 2.

The sampling surface E is formed in the central rectangular region 2 and band portions B1, B2 are formed in the side rectangular regions 4a, 4b.

In the feces sampling tool 1 of FIG. 5, the number of the water-soluble/water-disintegratable papers in the central rectangular area 2 is three, the number of water-soluble/water-disintegratable papers in the side rectangular areas 4a, 4b is two.

Figure 6:
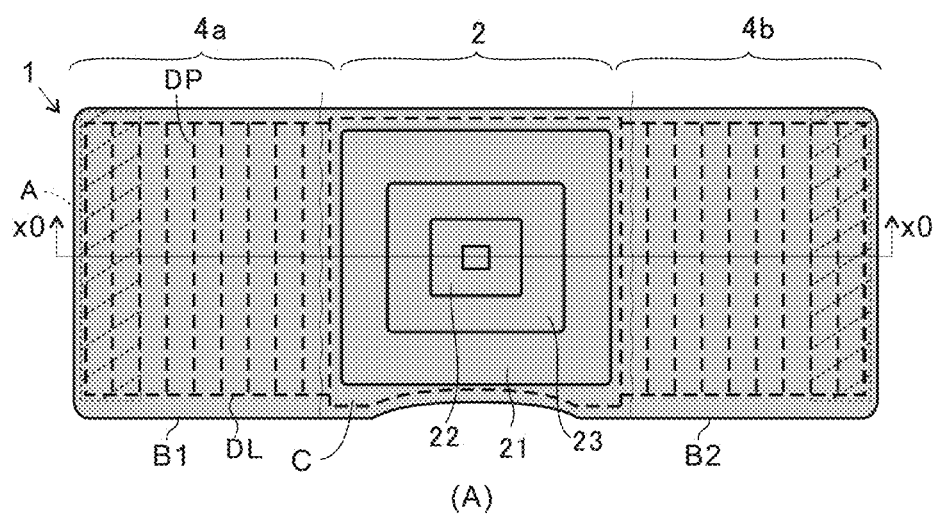
FIG. 6 is a view showing a third embodiment of the feces sampling tool according to the present invention.
Figure 6:
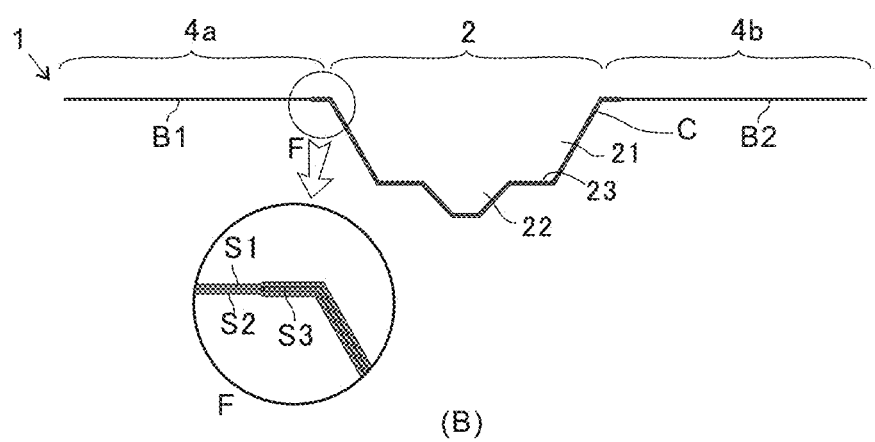

FIG. 6 (A) shows a plan view of the feces sampling tool. FIG. 6 (B) shows a sectional view of X0-X0 in (A). In FIG. 6 (B), extended a figure F is added.

In FIG. 6, the feces sampling tool 1 is comprised of the central rectangular areas 2 (a sampling portion) and a pair of the side rectangular areas 4a, 4b provided on either side of the central rectangular areas 2.

The cup body C included in the central rectangular area 2 is the same as the central rectangular area 2 (sampling unit) in FIG. 3.

The band portions B1, B2 constituting the side rectangular areas 4a, 4b are the same as those of the band portions B1, B2 in FIG. 3 except for the vertical width.

In FIG. 6, the hemming DL are formed around the cup body C and around the band portions B1, B2.

The hemming DL are formed of the broken lines shaped high press pressure portions.

Even more particularly, the pattern DP comprising the broken lines are formed in all of the band portions B1, B2.

In the feces sampling tool 1 of FIG. 6, like the feces sampling tool 1 of FIG. 1, due to the hemming DL or the pattern DP, water-soluble paper or water-disintegrable paper constituting the feces sampling tool 1 is difficult to peel off. Therefore, the strength of the cup C body and the band portion B1, B2 are kept.

Incidentally, the weight of the conventional feces sampling tool is about 6 grams or more. In contrast, the weight of the sampling tool 1 in FIGS. 1 to 6 is 4.5 g or less (furthermore, 4.0 g or less).

FIG. 7(A)-7(D) are drawings showing the use forms of the feces sampling tool 1 shown in FIGS. 1 to 6.

FIG. 7(A) is a plan view of the toilet stool 6, wherein the toilet seat 62 is flipped up.

FIG. 7(B) is a plan view of the toilet stool 6, wherein the toilet seat 62 is not flipped up.

FIG. 7(C) is a cross-sectional view (front view) taken along the line X 1-X 1 in FIG. 7(B).

FIG. 7(D) is a cross-sectional view (side view) taken along line X 2-X 2 in FIG. 7(B).

The left and right band portions B 1, B 2 of the feces sampling tool 1 are attached to the left and right of the upper edge of the rim portion 61 of the toilet stool 6, or to the left and right of the toilet seat.

As shown in FIGS. 7(A)-7(D), the end portions of the band portions B1 and B2 are attached to the toilet seat 62.

In the feces sampling tool 1 of FIG. 7 (A)-(D), the feces of the person 7 are sampled by the cup body C.

Figure 8:
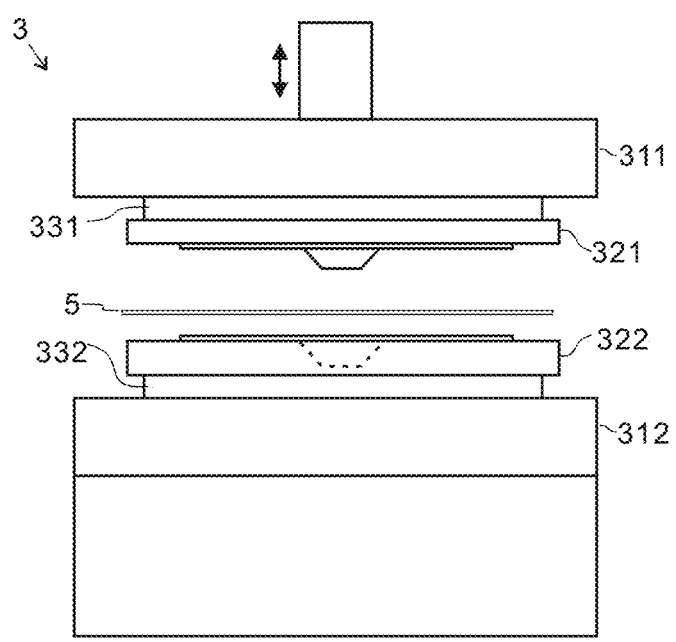
FIG. 8 is an explanatory view showing one embodiment of the feces sampling tool manufacturing apparatus.
Figure 9:
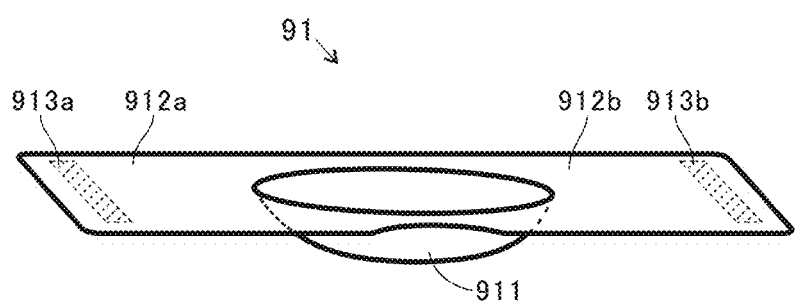
FIG. 9 is a view showing a conventional feces sampling tool.
Figure 10:
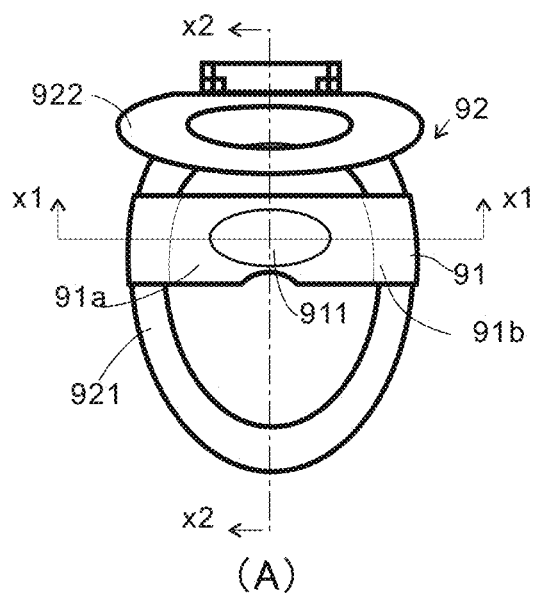
FIG. 10 is a view showing a usage mode of a conventional feces sampling tool.
Figure 10:
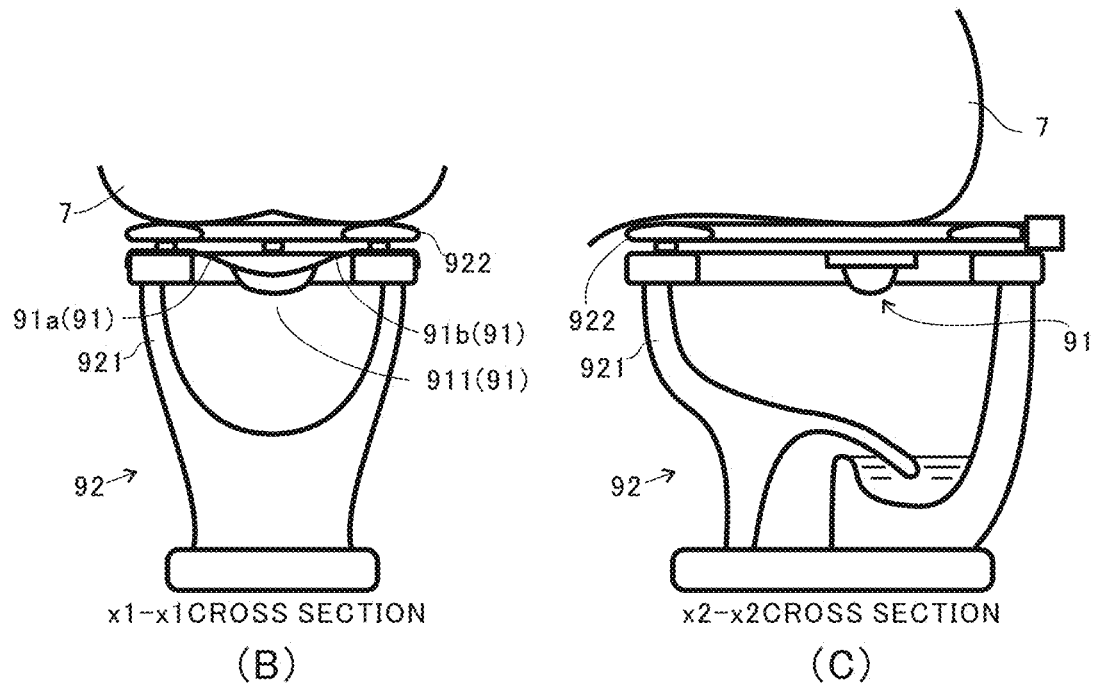

FIG. 8 shows one embodiment of the manufacturing apparatus 3 for the feces sampling tool 1 described above.

The manufacturing apparatus 3 includes the upper platen 311 and the lower platen 312, the upper die 321 and the lower die 322, the upper heater 331 and the lower heater 332.

The upper die 321 is provided on the upper platen 311 and the lower die 322 is provided in the lower turn table 312.

The upper heater 331 is provided between the upper platen 311 and the upper die 321, and the lower heater 332 is provided between the lower platen 312 and the lower die 322.

The upper heater 331 and the lower heater 332 are made of a high frequency line in which the side portion and the bottom portion are formed of a soft magnetic material.

A Litz wire is used for this high frequency line, a high frequency current of, for example, 10-30 KHz flows through the litz wire, and the upper die 321 and the lower die 322 are maintained at an appropriate temperature of 100-300 degree, for example.

A thin soft magnetic material can be used. As a result, the upper heater 331 and the lower heater 332 are lighter.

Hereinafter, a manufacturing method of the stone 1 using the manufacturing apparatus 3 shown in FIG. 8 will be described.

First, the raw material 5 to be processed is set between the upper die 321 and the lower die 322. For example, the upper die 321 is a male die, and the lower die 322 is a female die.

Then, the upper die 321 and the lower die 322 are closed, the raw material 5 is hot pressed, and at the same time, the periphery of the pressed raw material 5 is cut by a punching blade provided in the upper die 321.

As described above, an intermediate product of the tool 1 is manufactured.

By forming the adhesive layer A in this intermediate product, the feces sampling tool 1 is completed.

In the preliminary step of the hot press, at the same time as the hot press or in the post-heat pressing step, at least one of a deodorant, a deodorant, and a fragrance can be included (impregnated) in the handy equipment 1.

DENOTATION OF REFERENCE NUMERALS

1: feces sampling tool
2: central rectangular area
21: first stage
22: second stage
23: flange
3: manufacturing apparatus
311: upper platen
312: lower platen
321: upper die
322: lower die
331: upper heater
332: lower heater
4a, 4b: side rectangular area
5: raw material
6: toilet stool
61: rim portion
62: toilet seat
A: adhesive layer
B1, B2: band portion
C: cup body
DP: pattern
DL: hemming
E: sampling surface
H: watery feces discharge hole
S1, S2, S3: paper
W: wrinkle

The invention claimed is:

1. A feces sampling tool for use by a person on a toilet, the feces sampling tool comprising a sampling portion and two band portions symmetrically formed on left and right sides of the sampling portion,
   wherein the sampling portion and the band portions are made of one or a plurality of water-soluble or water-disintegrable paper,
   each part of the band portions is adapted to be stuck on left and right upper surfaces of a seat portion of the toilet or left and right upper surfaces of a rim portion of the toilet, whereby the sampling portion is suspended below the rim portion in a bowl portion of the toilet, and
   hemming is formed along a periphery of each of the band portions and along a periphery of the sampling portion of the sampling tool,
   wherein the hemming comprises at least one of creases and perforations,
   wherein the creases are lines in which portions with high pressing force, made by a die, appear continuously or intermittently, and
   wherein the perforations are lines in which cut portions, made by a die, appear intermittently.

2. The feces sampling tool according to claim 1, wherein the sampling portion has a planar shape area or a cup shape area.

3. A manufacturing apparatus for manufacturing a feces sampling tool according to claim 1, wherein the manufacturing apparatus includes:
   an upper platen and a lower platen,
   an upper die set on the upper platen,
   a lower die set on the lower platen, and
   at least one of an upper heater disposed between the upper platen and the upper die and a lower heater disposed between the lower platen and the lower die,
   wherein the upper heater and the lower heater are made of a high frequency line in which side portions and bottom portions are made of soft magnetic material.

4. The feces sampling tool according to claim 1, wherein hemming is also formed within the band portions in an orientation that runs parallel to a front-to-back direction of the feces sampling tool.

5. The feces sampling tool according to claim 1, wherein the sampling portion further comprises concentric rectangular surfaces that are parallel to the surfaces of the band portions.

6. The feces sampling tool according to claim 5, wherein the sampling portion resembles a pyramid-like structure.

7. The feces sampling tool according to claim 5, wherein the concentric rectangular surfaces comprise 3 concentric rectangular surfaces of decreasing size, with a largest concentric rectangular surface having the hemming and being in a same plane with the band portions, an intermediate concentric rectangular surface being smaller than and below the largest concentric rectangular surface, and a smallest concentric rectangular surface forming a bottom of the sampling portion.

8. The feces sampling tool according to claim 7, wherein the concentric rectangular surfaces are joined by angled vertical walls that form about 45-degree angles at the joints between each of the largest, intermediate, and smallest concentric rectangular surfaces.

9. A feces sampling tool for use by a person on a toilet, the feces sampling tool comprising a central sampling portion and left and right band portions symmetrically formed on respective left and right sides of the sampling portion,
   wherein the sampling portion and the band portions are made of one or a plurality of water-soluble or water-disintegrable paper sheets,
   wherein hemming is formed along a periphery of each of the band portions and along a periphery of the sampling portion of the sampling tool,
   wherein hemming is further formed within the band portions in an orientation that runs parallel to a front-to-back direction of the feces sampling tool,
   wherein the hemming comprises at least one of creases and perforations,
   wherein the creases are lines in which portions with high pressing force, made by a die, appear continuously or intermittently, and
   wherein the perforations are lines in which cut portions, made by a die, appear intermittently.

10. The feces sampling tool according to claim 9, wherein the sampling portion resembles a pyramid-like structure.

11. The feces sampling tool according to claim 9, wherein the sampling portion and the band portions are made of a same amount of water-soluble or water-disintegrable paper sheets.

12. The feces sampling tool according to claim 11, wherein the sampling portion and the band portions are made of 3 water-soluble or water-disintegrable paper sheets.

13. The feces sampling tool according to claim 9, wherein the sampling portion and the band portions are made of a different amount of water-soluble or water-disintegrable paper sheets.

14. The feces sampling tool according to claim 13, wherein the sampling portion is made of one more water-soluble or water-disintegrable paper sheet than that of the band portions.

15. The feces sampling tool according to claim 14, wherein the sampling portion is made of 3 water-soluble or water-disintegrable paper sheets and the band portions are made of 2 water-soluble or water-disintegrable paper sheets.

16. The feces sampling tool according to claim 9, wherein the creases and perforations are made by a die while the die is in a closed position.

* * * * *